US008617081B2

(12) United States Patent
Mestha et al.

(10) Patent No.: US 8,617,081 B2
(45) Date of Patent: Dec. 31, 2013

(54) ESTIMATING CARDIAC PULSE RECOVERY FROM MULTI-CHANNEL SOURCE DATA VIA CONSTRAINED SOURCE SEPARATION

(75) Inventors: Lalit Keshav Mestha, Fairport, NY (US); Survi Kyal, Rochester, NY (US); Gill Rafael Tsouri, Rochester, NY (US); Sohail A. Dianat, Pittsford, NY (US); Beilei Xu, Penfield, NY (US)

(73) Assignee: Xerox Corporation, Norwalk, CT (US)

(*) Notice: Subject to any disclaimer, the term of this patent is extended or adjusted under 35 U.S.C. 154(b) by 70 days.

(21) Appl. No.: 13/247,683

(22) Filed: Sep. 28, 2011

(65) Prior Publication Data

US 2013/0079649 A1 Mar. 28, 2013

(51) Int. Cl.
*A61B 5/02* (2006.01)
(52) U.S. Cl.
USPC .......................................................... 600/508
(58) Field of Classification Search
USPC .......... 600/508–528; 128/897–899, 905, 906, 128/915, 916, 920, 922–924
See application file for complete search history.

(56) References Cited

U.S. PATENT DOCUMENTS

2008/0319331 A1* 12/2008 Zizzo et al. .................... 600/511

OTHER PUBLICATIONS

Wei Lu et al., "Approach and Applications of Constrained ICA", IEEE Transactions on Neural Networks, vol. 16, No. 1, Jan. 2005.
Wei Lu, et al., "Constrained Independent Component Analysis", School of Computer Engineering, Nanyang Technological University, Singapore 639798.
Takano, et al., "Heart rate measurement based on a time-lapse image", Medical Engineering & Physics 29 (2007), pp. 853-857, www.sciencedirect.com.
Poh, et al., "Non-contact, automated cardiac pulse measurements using video imaging and blind source separation.", May 10, 2010, vol. 18, No. 10 / Optics Express 10762.
J. Lee, et al., "Temporally constrained ICA-based foetal ECG separation", Electronics Letters, Oct. 13, 2005, vol. 41, No. 21.
"Systems and Methods for Non-Contact Heart Rate Sensing", U.S. Appl. No. XX/XXX,XXX, concurrently filed.
Xu, Beilei, Lalit Keshav Mestha, Yao Rong Wang and Peter Paul, "A Multi-Layer Array for a Multi-Resolution Multi-Spectral Camera," U.S. Appl. No. 13/239,642, filed Sep. 22, 2011.
Yang, Ming, Qiong Liu, Thea Turner and Ying Wu, "Vital Sign Estimation from Passive Thermal Video," IEEE Conference on Computer Vision and Pattern Recognition, Jun. 2008, pp. 23-28.

(Continued)

*Primary Examiner* — Eric D. Bertram
*Assistant Examiner* — Elizabeth K So
(74) *Attorney, Agent, or Firm* — Philip E. Blair; Fleit Gibbons Gutman Bongini & Bianco P.L.

(57) ABSTRACT

What is disclosed is a system and method for recovering a patient's cardiac pulse rate from a sequence of video images recording of that patient. In one embodiment, a reference signal of a particular frequency is generated at predetermined frequency intervals and a constrained source separation is performed on the source data to obtain an estimation of the source signal intended to be recovered. The reference signal is updated and constrained source separation is again performed. These operations are repeated for all frequencies of the reference signal. The frequency at which a minimum error is achieved is determined to be the subject's recovered cardiac pulse frequency. In such a manner, the source signal is extracted and recovered reliably from captured multi-channel RGB signals or multispectral signals. The teachings hereof find their uses in a variety of medical solutions including various military, security and telemedicine applications. Various embodiments are disclosed.

21 Claims, 9 Drawing Sheets

(56) References Cited

OTHER PUBLICATIONS

Garbey, Marc, Nanfei Sun, Arcangelo Meria and Ioannis Pavlidis, "Contact-Free Measurement of Cardiac Pulse Based on the Analysis of Thermal Imagery," IEEE Transactions on Biomedical Engineering, Aug. 2007, vol. 54, No. 8, pp. 2-13.

Mestha, Lalit Keshav, Beilei Xu and Peter Paul, "Method for Classifying a Pixel of a Hyperspectral Image in a Remote Sensing Application," U.S. Appl. No. 13/023,310, filed Feb. 8, 2011.

Wang, Yao Rong, Zhigang Fan and Lalit Keshav Mestha, "Determining a Total Number of People in a IR Image Obtained Via an IR Imaging System," U.S. Appl. No. 12/967,775, filed Dec. 14, 2010.

Xu, Beilei, Whencheng Wu, Lalit Keshav Mestha and Graham Pennington, "System and Method for Object Identification and Tracking," U.S. Appl. No. 13/247,343, filed Sep. 28, 2011.

Lee, Jong-Hwan, Ho-Young Jung, Te-Won Lee and Soo-Young Lee, "Speech Coding and Noise Reduction Using Ice-Based Speech Features," in P. Pajunen and J. Karhunen (eds.), Proc. Second International Workshop on Independent Component and Analysis and Blind Signal Separation, 2000.

Hoyer, Patrik O. and Aapo Hyvärinen, "ICA Features of Colour and Stereo Images," P. Pajunen and J. Karhunen (eds.), Proc. Second International Workshop on Independent Component and Analysis and Blind Signal Separation, 2000, pp. 567-572.

Bell, Anthony J. and Terrence J. Sejnowski, "The "Independent Components" of Natural Science are Edge Filters," Vision Ref., 1997, vol. 37, No. 23, pp. 3327-3338.

Lee, Su-In and Serafim Batzoglou, "Application of independent component analysis to microarrays," Genome Biology, 2003, vol. 4, Issue 11, R76.

Cantelli, Mark, "Are you in There?" TOLLTRANS 2011, www.TrafficTechnologyToday.com.

\* cited by examiner

| VIDEO (CO-OPERATIVE) | TRUE | cICA RESOLUTION = 0.24 bpm BAND PASS = 0.75-2Hz STEP SIZE = 0.005 | GREEN SPECTRUM | ICA |
|---|---|---|---|---|
| V1 | 84 | 84.6 | 84.5 | 86.8 |
| V2 | 53 | 55.3 | 79.5 | 54.9 |
| V3 | 63 | 63.4 | 74.1 | 63.0 |
| V4 | 81 | 80.2 | 93.8 | 80.4 |
| V5 | 82 | 80.9 | 66.9 | 67.0 |
| V6 | 64 | 64.8 | 71.6 | 64.8 |
| V7 | 61 | 61.1 | 60.8 | 62.8 |
| V8 | 72 | 72.0 | 85.3 | 66.6 |
| V9 | 81 | 81.2 | 75.5 | 80.6 |
| V10 | 94 | 94.5 | 93.9 | 94.5 |
| V11 | 53 | 53.4 | 106.8 | 107.0 |

*FIG. 6*

| NON-COOPERATIVE) | TRUE HR | cICA RESOLUTION = 0.24 bpm BAND PASS = 0.75-2Hz STEP SIZE = 0.005 | GREEN SPECTRUM | ICA |
|---|---|---|---|---|
| V1(WTF) | 84 | 85.5 | 82.6 | 85.7 |
| V2(WTF) | 90 | 92.3 | 55.0 | 55.6 |
| V1(FT) | 84 | 85.3 | 69.1 | 69.6 |
| V2(FT) | 90 | 92.3 | 79.5 | 85.7 |

*FIG. 7*

| DISTANCE | TRUE | cICA | ICA |
|---|---|---|---|
| D1 | 103 | 105.4 | 105.5 |
| D2 | 100 | 101.5 | 101.3 |
| D3 | 102 | 100.6 | 70.7 |
| D4 | 100 | 93.8 | 88.5 |
| D5 | 104 | 73.1 | 69.6 |
| D6 | 102 | 62.8 | 69.4 |
| D7 | 105 | 90.7 | 83.3 |
| D8 | 77 | 91.2 | 48.1 |
| D9 | 74 | 60.7 | 60.6 |

FIG. 8

| DISTANCE | bd X ht | TRUE | cICA | ICA |
|---|---|---|---|---|
| D1 | 163 x 178 | 103 | 105.4 | 66.4 |
| D2 | 163 x 188 | 100 | 100.8 | 74.0 |
| D3 | 146 x 181 | 102 | 86.4 | 74.9 |
| D4 | 120 x 160 | 100 | 102.0 | 101.9 |
| D5 | 87 x 116 | 104 | 101.8 | 101.7 |
| D6 | 87 x 116 | 102 | 100.1 | 83.3 |
| D7 | 72 x 96 | 105 | 104.4 | 85.7 |
| D8 | 65 x 87 | 77 | 77.5 | 80.6 |
| D9 | 65 x 87 | 74 | 74.2 | 107.4 |

ESTIMATING CARDIAC PULSE RECOVERY FROM MULTI-CHANNEL SOURCE DATA VIA CONSTRAINED SOURCE SEPARATION

TECHNICAL FIELD

The present invention is directed to systems and methods for recovering an estimated cardiac pulse rate from a sequence of RGB or multi-spectral video image data captured from the facial/skin region of a person or animal being monitored for cardiac function in a remote sensing environment.

BACKGROUND

Assessment of cardio function is vitally important in monitoring neonatal patients, burn or trauma patients, sleep studies, and other cases where a continuous measurement of the heart rate is required. Currently, cardiac pulse is measured using an electrocardiogram (ECG) which often requires adhesive patches, spring loaded clips, chest straps, and the like, which may prove uncomfortable to patients over the long term. The ability to monitor a patient's physiological signals by non-contact means is highly desirable in the healthcare industry. Although non-contact methods may not be able to provide details concerning cardiac electrical conduction that ECG offers, non-contact methods effectuate long term patient monitoring of various physiological signals such as heart rate by acquiring data in an unobtrusive manner. Such technology further minimizes wire, cabling, and the like, which tend to be associated with patient monitoring devices.

Photoplethysmography (PPG) is one non-invasive electro-optic technique which senses a cardiovascular pulse wave (also referred to as "blood volume pulse") through variations in transmitted or reflected light. PPG provides valuable information about the cardiovascular system such as heart rate, arterial blood oxygen saturation, blood pressure, cardiac output, and autonomic function. PPG uses dedicated light sources but various studies have shown that pulse measurements can be acquired using normal ambient light as the illumination source. However, these efforts tend to rely on manual segmentation and heuristic interpretation of the captured raw images with minimal validation of performance characteristics. Furthermore, PPG is known to be susceptive to motion-induced signal corruption. In cases where the signal noise falls within the same frequency band as the physiological signal of interest, linear filtering with fixed cut-off frequencies can be rendered ineffective.

One technique for noise removal from physiological signals is blind source separation (BSS). BSS is a technique for the recovery of unobserved source signals from a set of observed mixed signals without any prior information being known about the "mixing" process. Typically, the observations are acquired from the output of a set of sensors where each sensor receives a different combination of source signals. Such methods acquire normal RGB signals from a CCD camera under normal ambient light and use BSS and Independent Component Analysis (ICA) to separate the source signals to detect pulse rate. Separating source signals using ICA on RGB signals can lead to errors due to the fact that the source can appear in any of the three outputs since the order in which the ICA returns the independent components will be random.

Accordingly, what is needed in this art are increasingly sophisticated systems and methods for recovering an estimated cardiac pulse rate from a sequence of RGB or multi-spectral video image data captured of a subject of interest being monitored for cardiac function in a remote sensing environment.

INCORPORATED REFERENCES

The following U.S. patents, U.S. patent applications, and Publications are incorporated herein in their entirety by reference.

"Systems And Methods For Non-Contact Heart Rate Sensing", U.S. patent application Ser. No. 13/247,575 which is commonly owned and concurrently filed herewith.

BRIEF SUMMARY

What is disclosed is a novel system and method for recovering an estimated cardiac pulse rate from a sequence of RGB or multi-spectral video image data recorded of a patient intended to be monitored for cardiac pulse rate determination. In various embodiments hereof, source video data is captured and a reference signal having predetermined frequency intervals is generated. Constrained source separation is performed on the source data to obtain an estimation of the source signal. The reference signal is updated and constrained source separation again performed. These operations are repeated for all frequencies of the reference signal until a convergence is detected. The error between the reference signal and the estimated output is then determined and the frequency at which a minimum error was achieved is determined to be the final cardiac pulse frequency. In such a manner, a source signal is reliably extracted from multi-channel source data. The teachings hereof improve pulse estimation accuracy with RGB and/or multi-spectral videos and advantageously find their uses in a wide variety of applications such as in telemedicine, emergency rooms, patient triage, intensive care and neonatal units, including an array of diverse military and security applications.

In one embodiment, the present method for cardiac pulse recovery and estimation from a video signal of a subject of interest, involves the following. First, video images captured of a person of interest intended to be monitored for cardiac function are received. The video images comprise multi-channel source data such as, RGB or multi-spectral signals. The captured source data is analyzed and pre-processed to isolate a facial/skin region within the video images. A reference signal is generated which has a frequency range which approximates the known frequency range of a cardiac pulse of the subject being monitored. The following operations are performed until a minimum error signal has been detected between the reference signal and the estimated source signal or a pre-defined number of operations have occurred. A) Compare the estimated source signal to the reference signal to determine whether a closeness has occurred to within a pre-defined threshold. B) If closeness has not occurred, then the reference signal is updated and the updated reference signal becomes the reference signal for the next iteration wherein a constrained source separation is again performed on the source data using the updated reference signal to obtain a next estimated source signal. A comparison is again made between the updated reference signal and the next estimated source signal to determine whether closeness has occurred. On this next iteration, if it is determined that closeness has not occurred then the reference signal is again updated and a next estimated source signal is produced. The process repeats until the desired measure of closeness has occurred or a pre-defined number of iterations have taken place. Upon completion of the above-described iterations, the frequency at which a minimum error was achieved is determined to be the subject's estimated cardiac pulse frequency. The estimated cardiac pulse frequency can then be communicated to a computer system, monitor, or a storage device for storage and/or further processing.

Many features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which:

FIG. 6 is Table 1 showing comparison results between cICA and prior art ICA methods under cooperative video capture mode;

FIG. 7 is Table 2 showing comparison results between cICA and prior art ICA methods under non-cooperative video capture mode;

FIG. 8 is Table 3 showing comparison results between cICA and ICA methods with respect to distance (without face tracking);

FIG. 9 is Table 4 showing comparison results between cICA and ICA methods with respect to distance (with face tracking);

DETAILED DESCRIPTION

Figure 1:
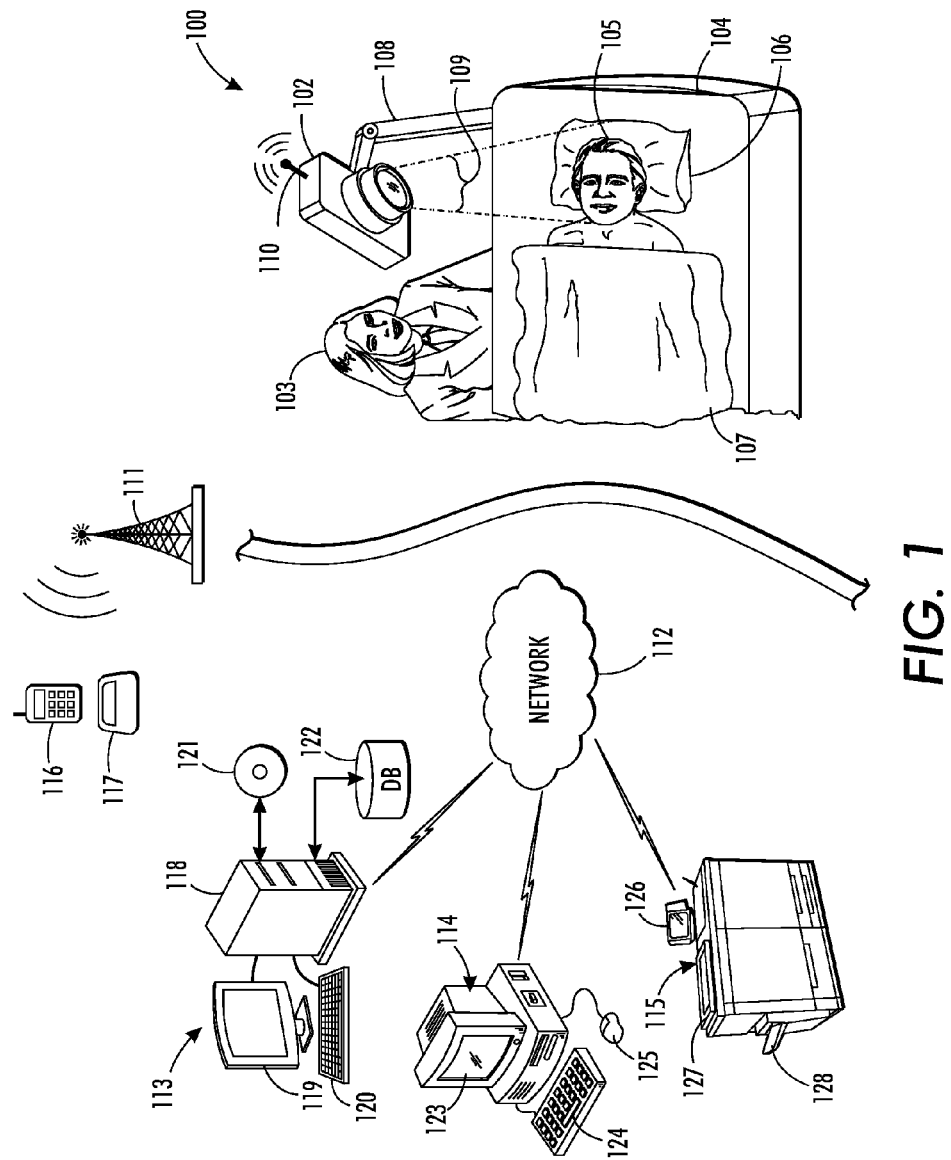
FIG. 1 illustrates one embodiment of a system for capturing RGB or multi-spectral signals of a subject of interest intended to be monitored for cardiac function.

What is disclosed is a system and method for recovering a patient's cardiac pulse rate from a sequence of video images recording of that patient. In one embodiment, a reference signal of a particular frequency is generated at predetermined frequency intervals and a constrained source separation is performed on the source data to obtain an estimation of the source signal intended to be recovered. The reference signal is iteratively updated and constrained source separation is again performed. Iterations are repeated for all frequencies of the reference signal until a measure of closeness has occurred to within a pre-defined threshold. The frequency at which a minimum error is achieved is determined to be the subject's recovered cardiac pulse frequency. In such a manner, the source signal can be extracted and recovered reliably for multi-channel source data such as RGB video. The teachings hereof find their uses in a variety of medical solutions including military and security applications. Various embodiments are disclosed.

It should be appreciated that one of ordinary skill in this art is familiar with various aspects of RGB and multi-spectral imaging and signal processing including methods and techniques involving Independent Component Analysis (ICA) as it pertains to the teachings disclosed herein.

Non-Limiting Definitions

A "subject of interest", as used herein, refers to a human being having a cardiac function for which a cardiac pulse frequency is intended to be determined using the teachings hereof. One example subject of interest shown as a patient in a hospital bed is shown at 105 of FIG. 1. It should be understood that, although the term "human", "person", or "patient" may be used throughout this text, the subject of interest intended to be monitored for cardiac function may be something other than a human such as, an animal or a reptile. Therefore, the explanatory use of the terms "person" or "patient" are not to be viewed as limiting the scope of the appended claims strictly to humans.

The term "pulse" was reportedly first described by the ancient Greek physician Claudius Galenus of Pergamum (known as "Galen") (AD 131-201). Although an antiquated term, it is still useful in the present age of computational analysis of cardiac physiology and performance. Pressure waves generated by the patient's heart (in systole) cause the arterial walls to move. This arterial movement can sensed by tactile methods and the pulse rate recorded in beats per minute (bpm). Heart rate is proportional to cardiac output, as described herein further.

A "frequency range of a subject's cardiac pulse" refers to the subject of interest's pulse over time. In humans, the frequency range is from about 50-240 bpm. An adult human heart rate is around 72 bpm. Each species has their own "normal" heart rate and thus their own cardiac pulse frequency range.

"Cardiac function" refers generally to the function of the subject's heart. In human, the heart is a left/right ventricular system for pumping blood. The left and right ventricles of the human heart operate interdependently. Cardiac function can be impacted by a variety of conditions and factors such as, for example, age, stress, cardiac health, overall health, and the like. Cardiac function can also be affected by environmental conditions such as altitude and pressure. One measure of cardiac function is cardiac output.

"Cardiac output" is the volume of blood the heart muscle can pump, expressed in L/min (normal ~5 L/min). Cardio Output can be expressed as: $CO=SV \cdot HR$, where SV is stroke volume, and HR is heart rate in bpm. Stroke volume can be affected by valvular dysfunction and ventricular geometric form.

"Updating the reference signal" means changing at least one aspect of the reference signal such as, for example, the frequency of the signal, or the signal's amplitude or phase, and may further include altering the wave form of the signal. The wave form can be, for example, a sine wave, a square wave, a user defined shape such as that obtained from an ECG signal, or a cardiac pulse wave form derived from apriori knowledge of the subject's cardiac history.

A "remote sensing environment" refers to non-contact, non-invasive sensing, i.e., the sensing device does not physically contact the person being sensed. The sensing device can be any distance away from the subject from, for example, as close as less than an inch to as far as miles (in the case of telemedicine). The environment may be any of a wide variety of settings where cardiac function is desired to be assessed using the teachings hereof such as, for example, a hospital, an ambulance, a medical office, and the like.

Basic Constrained Source Separation (cICA) Theory

Independent Component Analysis (ICA) is a statistical decomposition method for uncovering independent source signals from a set of observations that are composed of linear mixtures of the underlying sources. ICA defines a generative model wherein data variables are assumed to be linear mixtures of unknown latent variables, and the mixing system is also unknown. The latent variables are assumed to be non-Gaussian and mutually independent, and they are called "independent components" of the observed data. ICA uncovers the independent components (ICs) in the source signals by looking for statistically independent factors in the data (as opposed to uncorrelated factors). Also, the order of the resulting components is arbitrary. ICA defines the directions of the statistically independent components. The magnitudes of the ICs and the norms of the demixing matrix may be varied. In general, ICA has an inherent indeterminacy that cannot be reduced further without additional constraints. Eliminating indeterminacy in the permutation and dilation is useful to produce a unique solution with systematically ordered signals and a normalized demixing matrix.

Constrained source separation (cICA) separates a signal into its additive subcomponents using constraints to provide a solution with certain characteristics on the output. In practice, the ordering of the ICs is quite important to separate non-stationary signals or interested signals with significant statistical characters. Not all kinds of constraints can be used in cICA because some infringe classical ICA equivariant properties. The constraints should be selected and formulated to be consistent with the independence criteria. The subspace of the ICs is determined by a contrast function and nonlinear functions. Additional conditions can be incorporated using, for example, sparse decomposition of signals or fourth-order cumulants into the contrast function to help locate the global optimum separating the components. If the desired number of sources is unknown or the desired sources cannot be categorized according to density type, the subset recovered will not be useful.

cICA is essentially a constraint minimization, i.e., minimize function C(y) subject to constraints: g(y: W)≤0 and/or h(y: W)=0, where C(y) is a contrast function, and constraints:

$$g(y:W)=[g_1(y:W), g_2(y:W), \ldots, g_v(y:W)]^T$$

and $$h(y:W)=[h_1(y:W), h_2(y:W), \ldots, h_v(y:W)]^T$$

define the vectors of u (inequality) and v (equality), respectively. Statistical properties (e.g., consistency, asymptotic variance, robustness) of cICA depend on the choice of the contrast function C(y) and the constraints in the objective function. The constraints that define or restrict the properties of the independent components should not infringe the independence criteria.

More formally, let the time varying observed signal be: $x=(x_1, x_2, \ldots, x_n)^T$, where x is a linear mixture of ICs $c_i$ of a desired signal $c=(c_1, c_2, \ldots, c_m)^T$. Therefore, x=Ac where matrix A (of size nxm) represents the linearly mixed channels observing x. Demixing matrix W recovers components $c_1, c_2, \ldots, c_m$ of observed signal x which, in turn, produces signal y=Wx, given by: $y=(y_1, y_2, \ldots, y_m)^T$, with minimal knowledge of A and c.

For cICA, additional knowledge or data available about the desired source signals or mixing channels can be treated as apriori constraints to help guide the separation of the independent components. Reference signal $r=(r_1, r_2, \ldots, r_l)^T$ carries traces of information of desired signal c and need not to be exact to the original sources. A measure of closeness is estimated between signal $y_i$ and reference signal $r_i$ by the norm $\epsilon(y_i, r_i)$. The components of output signal y are mutually independent and correspond to/original sources mixed in observed signal x. Matrix A is an m×m square matrix. Demixing matrix W is l×m (l<m). The minimum norm $\epsilon(y_i, r_i)$ of all outputs y indicates that signal $y_i$ is closest to signal $r_i$. If this component is the one and only one closest to the reference signal then $\epsilon(y_i^*, r_i) < \epsilon(y_i^\circ, r_i)$, where $y_i = y_i^*$ is the output signal producing the desired independent component closest to $r_i$, and $y_i^\circ$ is the next closest output signal. cICA achieves the goal of recovering the closest independent component if the closeness measure and threshold are properly selected. Success depends on the selection of threshold parameter $\xi_i$: $\epsilon(y_i^*, r_i) - \xi_i \leq 0$. None of the other m−1 sources will correspond to $r_i$ if $\xi_i$ is in the scalar range of $[\epsilon(y_i^*, r_i), \epsilon(y_i^\circ, r_i)]$.

The interested reader is respectfully directed to the following texts which are incorporated herein in their entirety by reference. "*Independent Component Analysis*", Aapo Hyvärinen, Juha Karhunen, and Erkki Oja, Wiley-Interscience, 1st Ed. (2001), ISBN-13: 978-0471405405. "*Independent Component Analysis: Principles and Practice*", Stephen Roberts (Editor), Richard Everson (Editor), Cambridge University Press; 1st Ed. (2001), ISBN-13: 978-0521792981. "*Approach and Applications of Constrained ICA*", Wei Lu and Jagath C. Rajapakse, IEEE Transactions On Neural Networks, Vol. 16, No. 1, pp. 203-212, (January 2005).

Next will be described an example image capture system in an example hospital-like setting.

Example Image Capturing System

Reference is now being made to FIG. 1 which illustrates an example imaging system for capturing a multi-channel signal of a subject of interest.

The embodiment of FIG. 1 is shown generally comprising, on the right side of the figure, an examination room 100 having an example image capturing system 102 being operated by technician 103 standing at the side of bed 104 wherein lies subject 105 shown resting his/her head on pillow 106 while most of his/her body is partially covered by sheet 107. Camera system 102 is rotatably fixed to support arm 108 such that the camera's field of view 109 can be directed by nurse caregiver 103 onto the facial skin of patient 105. Support arm 108 is on a set of wheels so that the image capture system can be moved from bed to bed and room to room. Although patient 105 is shown in a prone position lying in a bed, it should be appreciated that images of the subject of interest can be captured while the subject is positioned in other supporting devices such as, for example, in a chair or wheelchair, standing up, including walking or moving. The embodiment of FIG. 1 is not intended to be viewed as limiting the scope of the appended claims in any respect.

Camera system 102 captures video images of the subject of interest to be monitored for cardiac function. The captured video images comprises multi-channel source data such as RGB and/or multi-spectral acquired over time. Camera 102 comprises imaging sensors which may be a single sensor or a sensor array including a plurality of individual or separate sensor units. A central processor integral to camera 102 and in communication with a memory (not shown) and the imaging sensor may take a variety of forms each having the capability of detecting changes in the status of sensors and outputting an alarm, notice, report, and the like if a change in any hardware or software of the camera has been detected. Other sensors contemplated are capable of sensing a change of position or status of subject 105 and issue an alarm or notification via transmission element 110 to a nurse, doctor, or technician in the event that the cardiac function of the patient falls outside a set of pre-defined parameters. Antenna 110 is used to communicate the captured images to various remote devices via a signal processor 111. Processor 111 receives the captured signals of subject 105 and communicates them to the various device shown on the left hand side of FIG. 1. Alternatively, transmitter 110 may be a wired (e.g., Ethernet) connection utilizing an Ethernet network consisting of Ethernet cables and an Ethernet hub that is in communication with tower 111 or with network 112. Of course, system 102 may include both wireless and Ethernet elements and may be connected via other means such as coaxial cable, electrical wires, radio frequency, Bluetooth, or any other manner for communicating data known in the art. Network 112 receives the transmitted signals from tower 111, and wirelessly communicates the received signal data to any of: workstation 113, graphical display device 114, and/or multi-function print system device 115. Signal transmission system 111 is also in wireless communication with handheld cellular device 116 and pager 117.

Workstation 113 and graphical display device 114 are in bi-directional communication with each other and multi-function devices 115 over network 112 including devices 116 and 117 and the image capture system 102. Such a networked environment may be wholly incorporated within the confines of a single building or buildings, such as a hospital center, or may be distributed to many different locations throughout an enterprise network. Many aspects of network 112 are commonly known and may include the World Wide Web. A further discussion as to the construction and/or operation of a specific network configuration has been omitted. Suffice it to say, data is transmitted in packets between networked devices via a plurality of communication devices and links using established protocols. Data is transferred in the form of signals which may be, for example, electronic, electromagnetic, optical, light, or other signals. These signals are provided to a communications device such as a server which transmits and receives data packets by means of a wire, cable, fiber optic, phone line, cellular link, RF, satellite, or other medium or communications pathway.

Computer 113 is shown comprising a computer case 118 housing therein a motherboard, CPU, memory, interface, storage device, and a communications link such as a network card. The computer system also includes a display 119 such as a CRT or LCD. An alphanumeric keyboard 120 and a mouse (not shown) provide a mechanism for the computer system to accept a user input. Computer readable media 121 contains machine executable instructions and other machine readable instructions for implementing the functionality and features of the present method.

In the embodiment shown, computer system 113 implements database 122 wherein various records are stored, manipulated, and retrieved in response to a query. Although the database is shown as an external device, the database may be internal to computer case 118 mounted on the hard disk therein. A record refers to any data structure capable of containing information which can be indexed, stored, searched, and retrieved in response to a query. Such constructs are well established in the software and database arts.

The computer platform is capable of running a server software program (or housing server hardware) for hosting installed applications. Such applications are readily available from vendors in various streams of commerce. The computer platform may be further capable of creating and running service proxies for directing requests for applications from a client device to the platform hosting the requested application and for redirecting responses from a host device to a requesting client device. The computer platform may act as a server to processors resident aboard a controller module residing within camera 102. The computer platform may alternatively be any of a laptop, server, mainframe, or the like. Device 114 is shown comprising display device 123 for the presentation of various captured images for visual review by a user such as technician 103. Device 114 also includes a keyboard 124 and mouse 125 to enable the manipulation of various images and including the reference signal(s) in accordance with the teachings hereof.

Multi-function device 115 is a print system having a user interface 126 for the visual display of images and for enabling the user to configure the device to any of a plurality of device-specific settings. Scanner 127 enables documents and images to be scanned into an electronic form and transmitted to another device over network 112. Paper tray 118 receives the printed outputs generated by the print system device. Multi-function device 115 is shown including a user interface (UI) 126 for the display thereon of icons and other selectable menu options and displayed information in response to an operation of the present method. The graphical UI includes a touch screen display for receiving user input via a touch-sensitive surface, and may further include any of a keyboard, keypad, mouse, touchpad, and the like. A display on the multi-function device is one of many possible displays retained in a memory associated with a user interface, including device-specific settings for instructing a control unit to adjust the multi-function device. The user interface includes controls for programming a range of values therefrom for carrying out various embodiments of the present method. The user interface further includes controls for programming the specific system settings of the device. Special purpose program instructions loaded on any of the networked devices causes a central processor of the computer to make any of the determinations or calculations, discussed with respect to the flow diagrams hereof, and provide the user with selectable menu options regarding error and minimum error, and make recommendations for adjustments to be made to the networked image capture system 102. Such program instructions and data records, and the like, may be retrieved by any of the networked devices from historical database 122.

All of the hardware devices of FIG. 1, including the camera system 102, collectively form a subnet. Techniques for placing devices in network communication are well established. Therefore, a further discussion as to techniques for placing such systems and devices in network communication has been omitted. Any of the networked devices may include a network interface card or system. Typical network interface cards enable one or more of the functionality of, for example, general purpose systems such as POTS (Plain Old Telephone System) and Integrated Services Digital Network (ISDN) and/or special purpose systems such as a Local Area Network (LAN) and Wide Area Network (WAN). It should be appreciated that any of the devices 113-117 of FIG. 1 can be placed in communication with any of the other devices shown in the networked configuration including with image capture system 102.

Example Block Diagram

Figure 2:
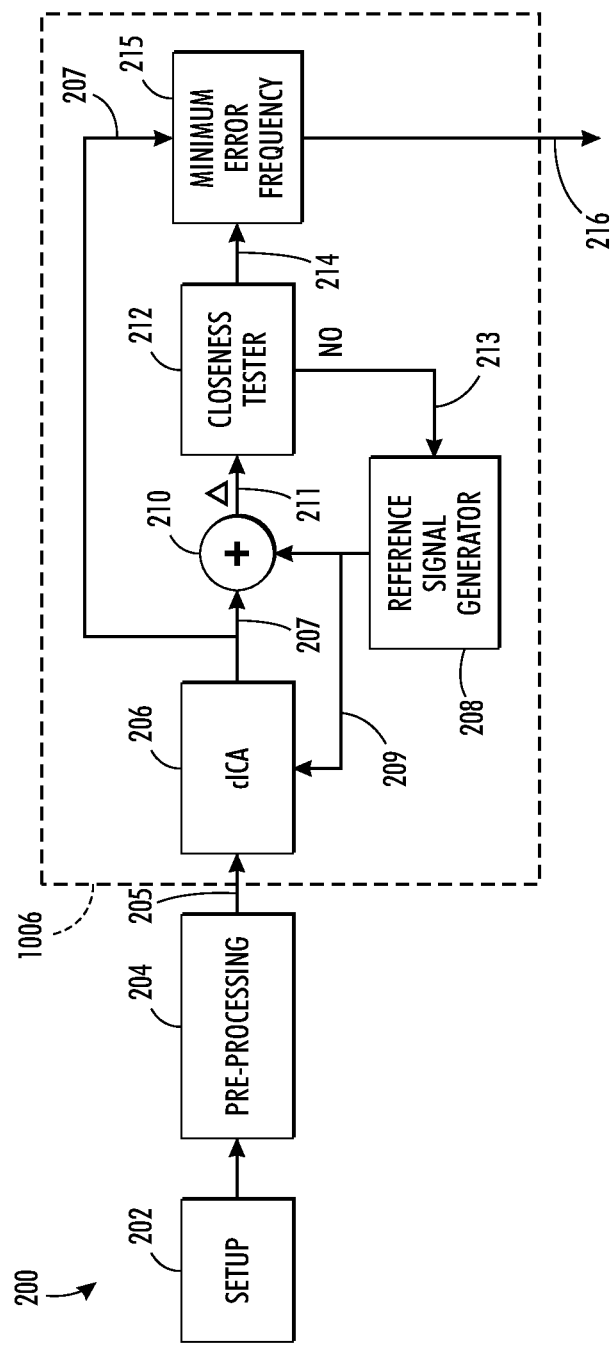
FIG. 2 illustrates a block diagram of one embodiment of the present system and method for cardiac pulse frequency recovery and estimation.

Reference is now being made to FIG. 2 which illustrates a block diagram of one embodiment of the present system and method for cardiac pulse frequency recovery and estimation.

System 200 of FIG. 2 is shown including an initialization setup 202 wherein various parameters are defined such as, for example, the number of frames to be captured, a time duration for the video sequence, a desired field of view, a location of the facial region of the subject of interest, and the like. Upon the completion of the system setup and configuration, multi-channel signals are captured and pre-processed 204 wherein the captured video images are received or otherwise retrieved from a memory or storage device and portions of the captured images are extracted from the video sequence. Since the present system and method is directed to extracting an estimated cardiac pulse frequency from a multi-channel signal, the patient's facial region or skin area is preferably isolated in the image sequence using, for example, facial recognition algorithms or multi-spectral skin-detection techniques which detect exposed facial skin areas in an image. The above-described parameters are used by the pre-processing unit to identify the number of frames, the width, height, duration and frame rate for skin detection and signal extraction. Skin isolation is important because, during the cardiac cycle, slight changes occur in blood vessels present underneath the skin. By recording video images of the subject's skin where higher concentrations of blood vessels exist such as in the face and neck, relatively small changes in blood vessels are registered as reflected signals comprising a mixture of plethysmographic signals along with artifacts such as involuntary and voluntary bodily motions and fluctuations due to, for example, ambient illumination. Human skin reflects certain wavelengths of light differently than, for instance, fabrics or other materials. Pre-processing further includes normalizing or centering, continuous time band pass filtering (with a bandwidth of 0.75-2 Hz) and whitening. Bandwidth can be adjusted based on the patients pulse rate. For infants, the upper limit can be as high as 4 Hz. Average RGB values of pixels of exposed skin in each frame are converted to a zero-mean unit variance signal at a corresponding time. The whitened source data 205 is provided to cICA module 206 wherein a time history of signals is processed by using the above-described constrained source separation method to separate the underlying pulse signal and produce an estimated source signal.

Figure 5A:
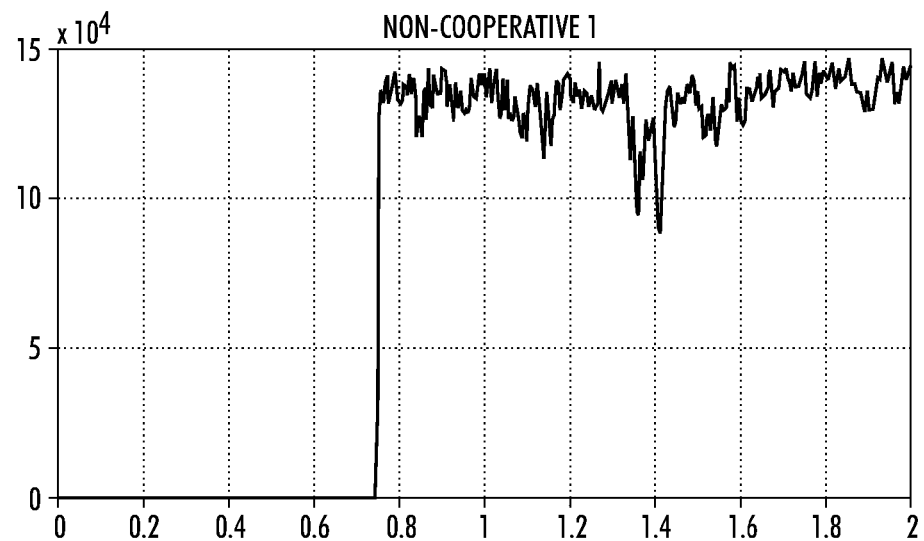
FIG. 5 are examples of power spectra of the error between the cICA estimated output signal and the reference frequency.
Figure 5B:
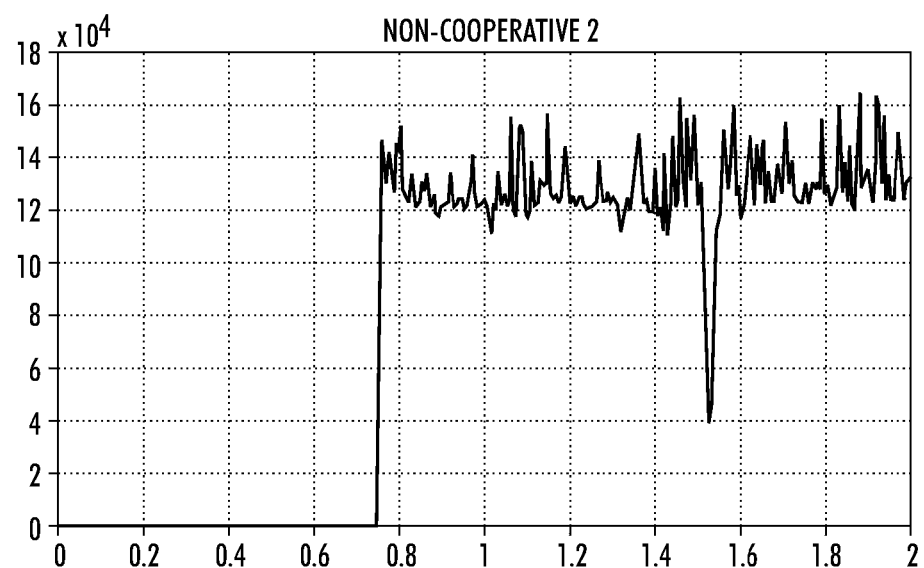

Signal generator 208 generates a reference signal 209 having a frequency range which approximates a frequency range of the subject's cardiac pulse. The generated reference signal is provided to cICA 206 and, on each iteration, is compared by comparator 210 against the produced estimated source signal 207 such that a difference 211 therebetween is determined. Examples of the power spectra of the error between the estimated output signal and the reference frequency are shown in FIG. 5. Closeness test module 212 uses difference 211 to determine whether reference signal 209 and estimated source signal 207 are with a pre-defined threshold. If it is determined that closeness has not occurred then a signal 213 is sent to signal generator 208 to output an updated reference signal 209. The reference signal can be updated by changing various aspects of the signal such as, for example, the frequency, amplitude, phase, or the wave form. The updated reference signal is again provided to cICA 206 which produces an updated estimated source signal 207. One of ordinary skill will recognize the iterative nature of FIG. 2. Updated estimated source signal 207 is again compared to the updated reference signal 209 and the result 211 is provided to closeness tester 212 to determine whether closeness has occurred. If closeness has not occurred then iterations repeat until the closeness criteria has been met or a defined number of iterations have occurred. Upon detection of closeness, a signal 214 is provided to minimum error frequency processor 215 to capture the last estimated source signal 207 (determined on the last iteration) and analyze the estimated source signal to determine the frequency at which the minimum error was achieved. The frequency at which the minimum error was achieved is the subject's recovered pulse frequency 216.

Flow Diagram of One Example Embodiment

Figure 3:
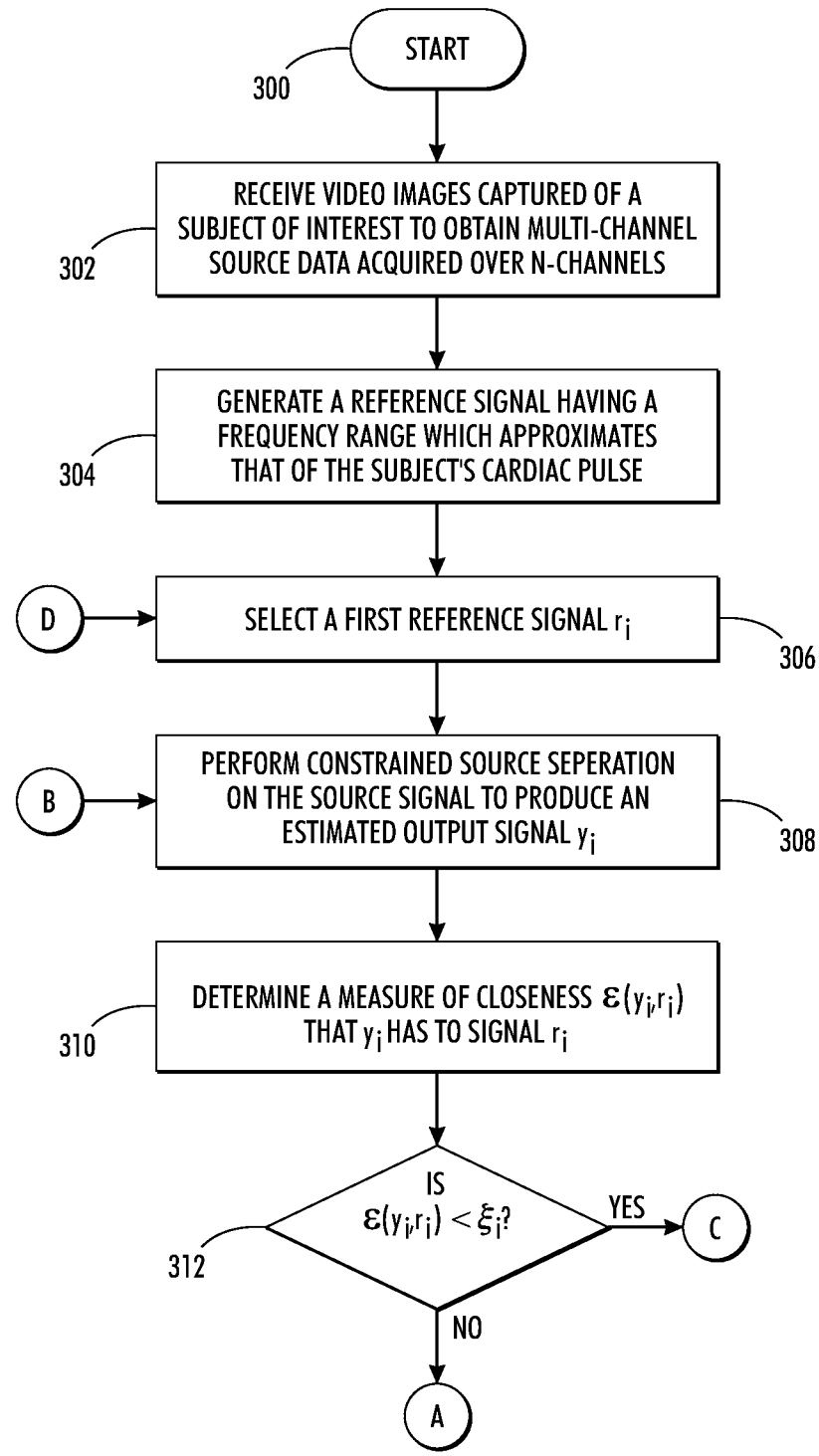
FIG. 3 is a flow diagram of one embodiment of the present method for cardiac pulse recovery and estimation from a video signal of a subject of interest.

Reference is now being made to the flow diagram of FIG. 3 which illustrates one embodiment of the present method for cardiac pulse recovery and estimation from a video signal captured of a subject of interest. Flow processing starts at step 300 and immediately proceeds to step 302.

At step 302, receive video images which have been captured of a subject of interest intended to be monitored for cardiac function. The video images comprise a time varying source signal $x=(x_1, x_2, \ldots, x_n)^T$, acquired over n channels. One example system for multi-channel source data of such video images is shown and discussed with respect to the example embodiment of FIG. 1.

At step 304, generate a reference signal $r=(r_1, r_2, \ldots, r_l)^T$ which has a frequency range which approximates a frequency range of the subject's cardiac pulse. The reference signal can be received from a remote device over a networked computing environment such as that shown in FIG. 1 or retrieved from a memory, storage device, or obtained from a database of reference signals.

At step 306, select a first reference signal $r_i$ for processing.

At step 308, perform constrained source separation on source signal x using the current reference signal $r_i$ to produce an estimated source signal $y_i$.

At step 310, determine a measure of closeness $\epsilon(y_i, r_i)$ that output signal $y_i$ has to reference signal $r_i$.

At step 312, a determination is made whether the closeness measure $\epsilon(y_i, r_i)$ is less than or equal to a pre-defined threshold $\xi_i$. If at step 312, the closeness measure indicates that a closeness has not occurred then processing continues with respect to node A (of FIG. 4) wherein, at step 314, at least one aspect of the reference signal is changed. Processing then continues with respect to node B wherein, at step 308, constrained source separation is again performed on the source data using the modified reference signal and closeness is again tested. The process repeats until either closeness has occurred or a pre-defined number of iterations have taken place. If, at step 312, $\epsilon(y_i, r_i) \leq \xi_i$, then a closeness has occurred, then processing continues with respect to node C wherein, at step 316, a determination is made whether any more reference signals remain to be processed. If so, then processing continues with respect to node D wherein, at step 306, a next reference signal is selected or otherwise identified for processing and the method repeats until all the reference signals $r_i$ have been processed accordingly.

At step 318, determine a minimum value of $\epsilon(y_i, r_i)$ for all estimated output signals $y=(y_1, y_2, \ldots, y_l)^T$ such that $\epsilon(y_i, r_i) < \epsilon(y_i^o, r_i)$, where $y_i^*$ is the output signal having a frequency which best estimates the subject's cardiac frequency.

At step 324, communicate the final estimated cardiac frequency to a computer system for display on a monitor device or for storage to a memory or storage device. In this embodiment, the process ends upon communication of the final estimated cardiac frequency. The final estimated cardiac frequency can be, for example, plotted and printed on the multi-function device of FIG. 1, or communicated to a physician's cell phone or paging device.

It should be appreciated that the flow diagrams hereof are illustrative. One or more of the operative steps illustrated in any of the flow diagrams may be performed in a differing order. Other operations, for example, may be added, modified, enhanced, condensed, integrated, or consolidated with the steps thereof. Such variations are intended to fall within the scope of the appended claims. All or portions of the flow diagrams may be implemented partially or fully in hardware in conjunction with machine executable instructions.

Performance Results

To illustrate the effect of cICA, video recordings were produced using a standard 2 MP RGB Logitech camera at 15 frames per second (fps) with pixel resolution of 320×240 and saved in WMV format. Participants were between the ages of 18-45 years and from different nationalities. The accuracy of heart rate measurements obtained using ICA were first analyzed for accuracy. The cICA was then applied to the same set of data. Error between estimated heart rate to FDA approved sensor is further reduced by this new methodology (Tables [1-4]). All heart rate numbers are shown in beats per minute.

FIG. 5 shows examples of power spectra of error signals with respect to frequency for cooperative and non-cooperative capture modes. This demonstrates that the present method is motion tolerant and performs well even if the video is taken from a distance. Moreover, the method is easily scalable for multiple people in front of the camera.

Table 1 (FIG. 6) is a comparison between cICA and prior art methods under cooperative video capture mode.

Table 2 (FIG. 7) is a comparison between cICA and prior art methods under non-cooperative video capture mode. WFT is without face tracking and FT means with face tracking.

Table 3 (FIG. 8) is a comparison between cICA and ICA methods with respect to distance (without face tracking).

Table 4 (FIG. 9) is a comparison between cICA and ICA methods with respect to distance (with face tracking).

Example Functional Block Diagram

Figure 4:
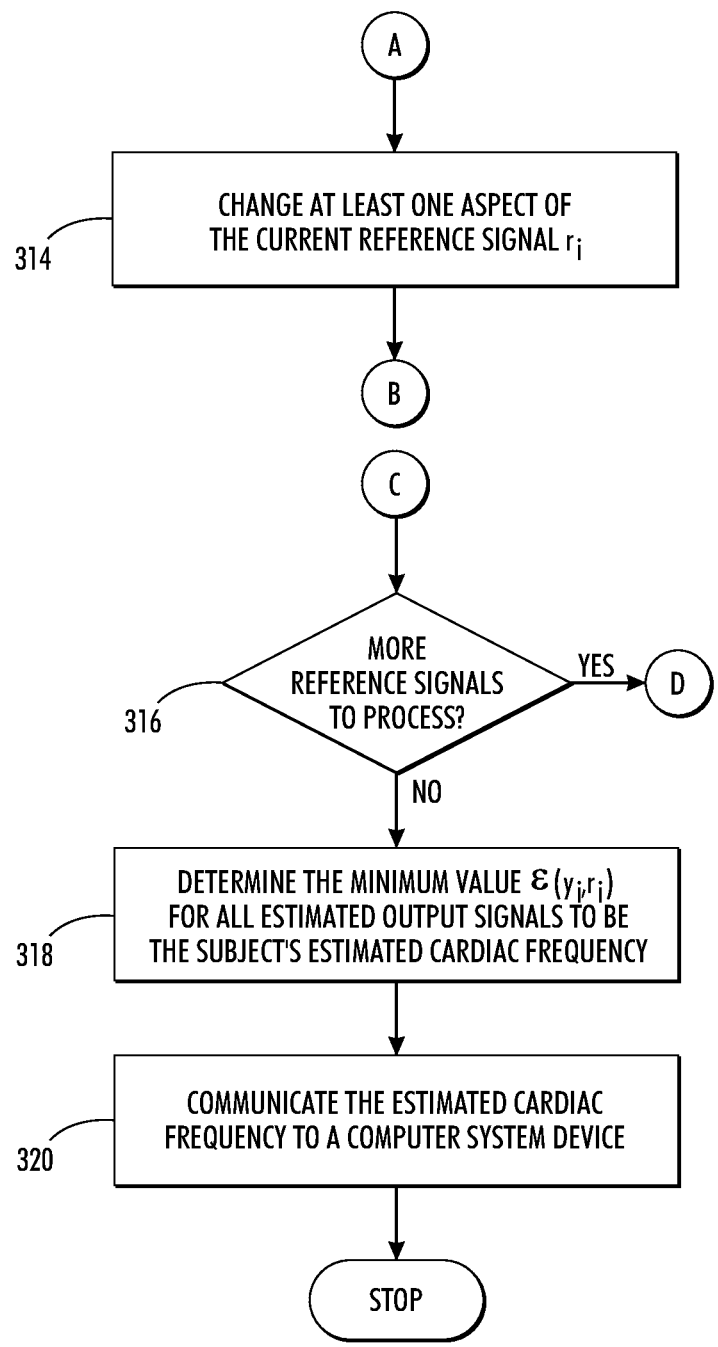
FIG. 4 is a continuation of the flow diagram of FIG. 3 with flow processing continuing with respect to node A.
Figure 10:
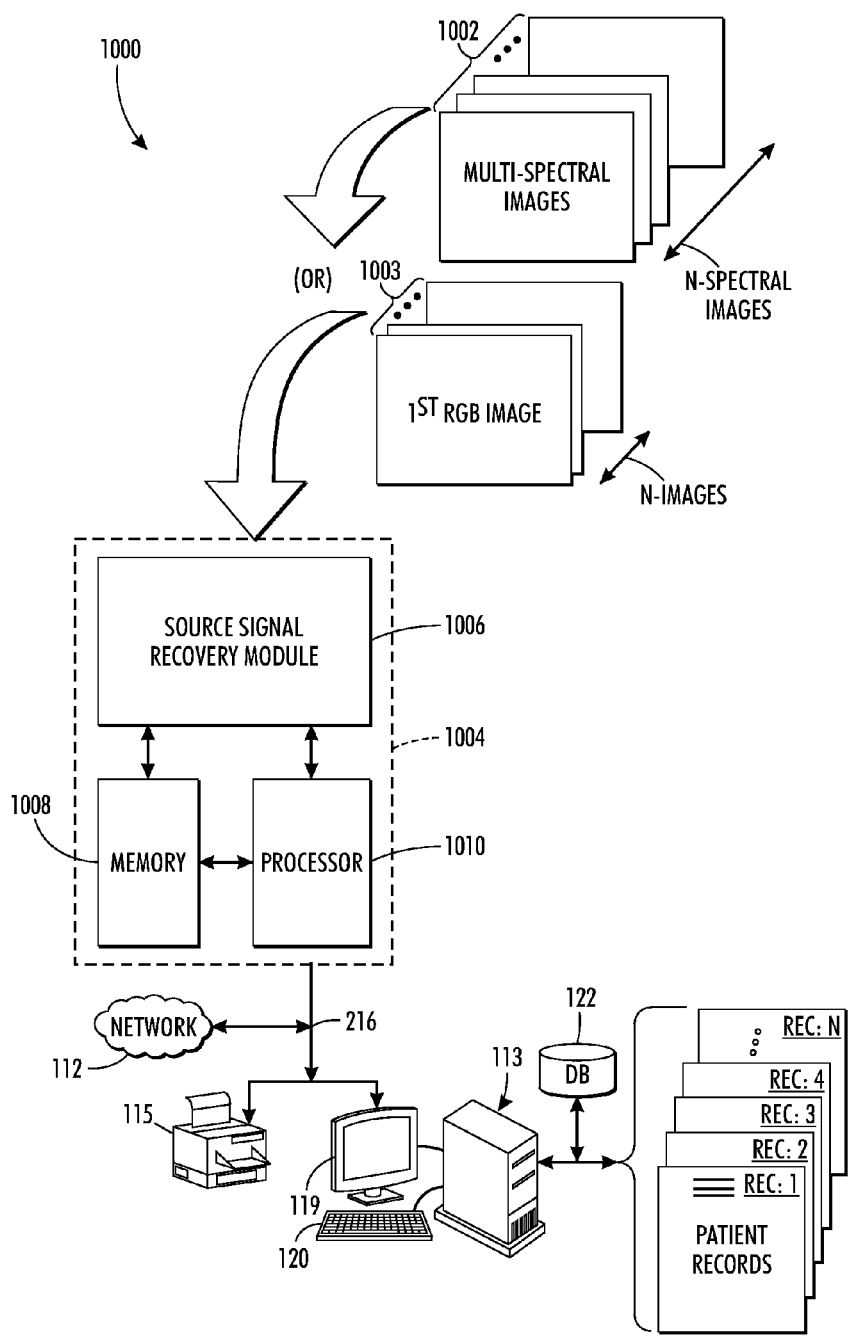
FIG. 10 illustrates a block diagram of one example processing system capable of implementing various aspects of the present method shown and described with respect to the flow diagrams of FIGS. 3 and 4.

Reference is now being made to FIG. 10 which illustrates a block diagram of one example processing system 1000 capable of implementing various aspects of the present method described with respect to the flow diagrams of FIGS. 3 and 4.

The embodiment of FIG. 10 receives a sequence of video images captured of a subject of interest intended to be monitored for cardiac function. In FIG. 10, the captured video images are either a plurality of multi-spectral images 1002 captured using a multi-spectral camera or a plurality of RBG images captured using a standard 3-channel camera. The sequence of images collectively comprises a multi-channel source data acquired over a duration of time. Signal processing system 1004 receives the multi-channel source data into source signal recovery module 1006 which performs all the functionality as describe in FIG. 2. Memory 1008 and CPU 1010 facilitate all of the processing and outputs the final estimated cardiac frequency 216. The final estimated cardiac frequency 216 is communicated to a workstation 113 as shown and described with respect to FIG. 1. Patient information can be stored and/or retrieved to any of the records in database 122.

It should be understood that any of the modules and processing units of FIG. 10 are in communication with workstation 113 via pathways (not shown) and may further be in communication with one or more remote devices over network 112. It should be appreciated that some or all of the functionality for any of the modules of system 1004 may be performed, in whole or in part, by components internal to workstation 113 or by a special purpose computer system. It should also be appreciated that various modules may designate one or more components which may, in turn, comprise software and/or hardware designed to perform the intended function. A plurality of modules may collectively perform a single function. Each module may have a specialized processor capable of executing machine readable program instructions. A module may comprise a single piece of hardware such as an ASIC, electronic circuit, or special purpose processor. A plurality of modules may be executed by either a single special purpose computer system or a plurality of special purpose computer systems in parallel. Connections between modules include both physical and logical connections. Modules may further include one or more software/hardware modules which may further comprise an operating system, drivers, device controllers, and other apparatuses some or all of which may be connected via a network. It is also contemplated that one or more aspects of the present method may be implemented on a dedicated computer system and may also be practiced in distributed computing environments where tasks are performed by remote devices that are linked through a network.

Example Special Purpose Computer

Figure 11:
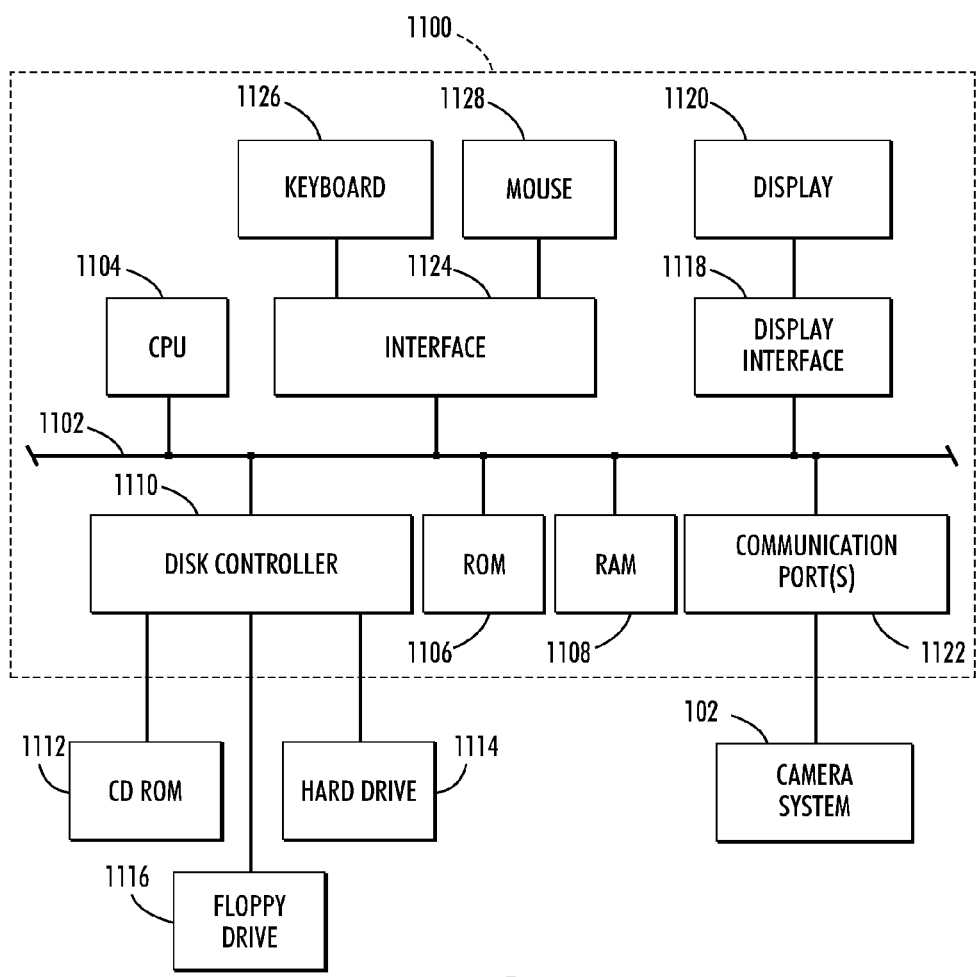
FIG. 11 illustrates a block diagram of one example special purpose computer for implementing one or more aspects of the present method as described with respect to the flow diagrams of FIGS. 3 and 4, and the block diagram of FIG. 10.

Reference is now being made to FIG. 11 which illustrates a block diagram of one example special purpose computer 1100 for implementing one or more aspects of the present method as described with respect to the flow diagrams of FIGS. 3 and 4, and the modules and processing units of the block diagram of FIG. 10. Such a special purpose processor is capable of executing machine executable program instructions and may comprise any of a micro-processor, microcontroller, ASIC, electronic circuit, or any combination thereof.

In FIG. 11, communications bus 1102 is in communication with a central processing unit (CPU) 1104 capable of executing machine readable program instructions for performing any of the calculations, comparisons, logical operations, and other program instructions for performing any of the steps described above with respect to the flow diagrams and illustrated embodiments hereof. Processor 1104 is in communication with memory (ROM) 1106 and memory (RAM) 1108 which, collectively, constitute example storage devices. Such memory may be used to store machine readable program instructions and other program data and results to sufficient to carry out any of the functionality described herein. Disk controller 1110 interfaces with one or more storage devices 1114 which may comprise external memory, zip drives, flash memory, USB drives, or other devices such as CD-ROM drive 1112 and floppy drive 1116. Storage device stores machine executable program instructions for executing the methods hereof. Such storage devices may be used to implement a database wherein various records are stored. Display interface 1118 effectuates the display of information on display 1120 in various formats such as, for instance, audio, graphic, text, and the like. Interface 1124 effectuates a communication via keyboard 1126 and mouse 1128, collectively a graphical user interface. Such a graphical user interface is useful for a user to enter information about any of the displayed information in accordance with various embodiments hereof. Communication with external devices may occur using example communication port(s) 1122. Such ports may be placed in communication with any of the example networks shown and described herein, such as the Internet or an intranet, either by direct (wired) link or wireless link, as shown and discussed with respect to the networked configuration of FIG. 1. Example communication ports include modems, network cards such as an Ethernet card, routers, a PCMCIA slot and card, USB ports, and the like, capable of transferring data from one device to another. Software and data is transferred via the communication ports in the form of signals which may be any of digital, analog, electromagnetic, optical, infrared, or other signals capable of being transmitted and/or received by the communications interface. Such signals may be implemented using, for example, a wire, cable, fiber optic, phone line, cellular link, RF, or other signal transmission means presently known in the arts or which have been subsequently developed.

It will be appreciated that the above-disclosed and other features and functions, or alternatives thereof, may be desirably combined into many other different systems or applications. Various presently unforeseen or unanticipated alternatives, modifications, variations, or improvements therein may become apparent and/or subsequently made by those skilled in the art which are also intended to be encompassed by the following claims. Accordingly, the embodiments set forth above are considered to be illustrative and not limiting. Various changes to the above-described embodiments may be made without departing from the spirit and scope of the invention. The teachings hereof can be implemented in hardware or software using any known or later developed systems, structures, devices, and/or software by those skilled in the applicable art without undue experimentation from the functional description provided herein with a general knowledge of the relevant arts. Moreover, the methods hereof can be implemented as a routine embedded on a personal computer or as a resource residing on a server or workstation, such as a routine embedded in a plug-in, a driver, or the like. The methods provided herein can also be implemented by physical incorporation into an image processing or color management system. Furthermore, the teachings hereof may be partially or fully implemented in software using object or object-oriented software development environments that provide portable source code that can be used on a variety of computer, workstation, server, network, or other hardware platforms. One or more of the capabilities hereof can be emulated in a virtual environment as provided by an operating system, specialized programs or leverage off-the-shelf computer graphics software such as that in Windows, Java, or from a server or hardware accelerator or other image processing devices.

One or more aspects of the methods described herein are intended to be incorporated in an article of manufacture, including one or more computer program products, having computer usable or machine readable media. The article of manufacture may be included on at least one storage device readable by a machine architecture embodying executable program instructions capable of performing the methodology described herein. The article of manufacture may be shipped, sold, leased, or otherwise provided separately either alone or as part of an add-on, update, upgrade, or product suite. It will be appreciated that various of the above-disclosed and other features and functions, or alternatives thereof, may be combined into other systems or applications. Various presently unforeseen or unanticipated alternatives, modifications, variations, or improvements therein may become apparent and/or subsequently made by those skilled in the art which are also intended to be encompassed by the following claims. Accordingly, the embodiments set forth above are considered to be illustrative and not limiting. Various changes to the above-described embodiments may be made without departing from the spirit and scope of the invention. The teachings of any printed publications including patents and patent applications, are each separately hereby incorporated by reference in their entirety.

What is claimed is:

1. A method for cardiac pulse recovery and estimation from a video images captured of a subject of interest, the method comprising:
   receiving video images captured of a subject of interest being monitored for cardiac function, said video images comprising source video data wherein at least one time varying cardiac source signal is embedded, said video images having been acquired over multiple channels of a video imaging device;
   generating a set of reference signals having a frequency range which approximates a frequency range of said subject's cardiac pulse;
   performing, using said set of reference signals, a constrained source separation on said source video data to obtain a first estimated source signal;
   for each reference signal:
      A) performing a constrained source separation on said source data to obtain a next estimated source signal;
      B) comparing said reference signal to said next estimated source signal; and
      repeating A thru B until all reference signals have been compared at least once;
   selecting an estimated source signal having a minimum error between the estimated source signal and a corresponding reference signal; and
   communicating at least one aspect of said selected estimated source signal to a computer system.

2. The method of claim 1, wherein a frequency at which said minimum error was achieved being the estimated cardiac frequency of said subject.

3. The method of claim 1, wherein said minimum error was achieved by adjusting phase of the estimated source signal and calculating a difference between two waveforms.

4. The method of claim 1, further communicating at least one aspect of said cardiac source signal to said computer system.

5. The method of claim 1, wherein said acquired source signal comprises any of: RGB signals, and multi spectral signals.

6. The method of claim 1, wherein said video images are obtained in a non-contact environment.

7. The method of claim 6, wherein said non-contact environment is for remote sensing as in telemedicine.

8. The method of claim 1, wherein, as a result of said comparison, changing at least one aspect of said reference signal by changing a wave form, wherein said wave form comprises any of: a sine wave, a square wave, a user defined shape such as that obtained from an ECG signal, and a cardiac pulse wave form derived from said subject.

9. The method of claim 1, wherein said frequency range of a human cardiac pulse comprises 50 beats per minute to 240 beats per minute.

10. The method of claim 1, further comprising:
    determining a region of human skin in said received video images; and
    isolating said determined human skin region for processing such that slight volumetric changes occurring in blood vessels due to cardiac function underneath the skin during a cardiac cycle can be analyzed.

11. A system for cardiac pulse recovery and estimation from a video images captured of a subject of interest, the system comprising:
    a memory; and
    a processor in communication with said memory, said processor executing machine readable instructions for performing:
       receiving video images captured of a subject of interest intended to be monitored for cardiac function, said video images comprising source video data wherein at least one time varying cardiac source signal is embedded, said video images having been acquired over multiple channels of a video imaging device;
       generating a set of reference signals having a frequency range which approximates a frequency range of said subject's cardiac pulse;

performing, using said set of reference signals, a constrained source separation on said source video data to obtain a first estimated source signal;

for each reference signal:
- A) performing a constrained source separation on said source data to obtain a next estimated source signal;
- B) comparing said reference signal to said next estimated source signal; and
- repeating A thru B until all reference signals have been compared at least once;

selecting an estimated source signal having a minimum error between the estimated source signal and a corresponding reference signal; and communicating at least one aspect of said selected estimated source signal to a computer system.

12. The system of claim 11, wherein a frequency at which said minimum error was achieved being the estimated cardiac frequency of said subject.

13. The system of claim 11, wherein said minimum error was achieved by adjusting phase of the estimated source signal and calculating a difference between two waveforms.

14. The system of claim 11, wherein said acquired source signal comprises any of: RGB signals, and multi-spectral signals.

15. The system of claim 11, wherein said video images are obtained in a non-contact environment.

16. The system of claim 15, wherein said non-contact environment is for remote sensing as in telemedicine.

17. The system of claim 11, wherein, as a result of said comparison, changing at least one aspect of said reference signal by changing any of: a frequency, an amplitude, a phase, and a wave form of said reference signal.

18. The system of claim 17, wherein said wave form comprises any of: a sine wave, a square wave, a user defined shape such as that obtained from an ECG signal, and a cardiac pulse wave form derived from said subject.

19. The system of claim 11, wherein said frequency range of a human cardiac pulse comprises 50 beats per minute to 240 beats per minute.

20. The system of claim 11, wherein said threshold is selected to be in a scalar range of said subject's cardiac pulse rate.

21. The system of claim 11, further comprising:
- determining a region of human skin in said received video images; and
- isolating said determined human skin region for processing such that slight volumetric changes occurring in blood vessels due to cardiac function underneath the skin during a cardiac cycle can be analyzed.

* * * * *